United States Patent
Zhao et al.

(10) Patent No.: US 8,771,484 B2
(45) Date of Patent: Jul. 8, 2014

(54) DEVICE FOR DETERMINATION OF PARAMETERS OF PARTICLES IN CONDUCTIVE SOLUTION AND MICROSCOPIC HOLE ASSEMBLY

(75) Inventors: Tianfeng Zhao, Shenzhen (CN); An Li, Shenzhen (CN); Huaming Xu, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 1247 days.

(21) Appl. No.: 11/615,480

(22) Filed: Dec. 22, 2006

(65) Prior Publication Data
US 2008/0093216 A1 Apr. 24, 2008

(30) Foreign Application Priority Data
Oct. 18, 2006 (CN) .......................... 2006 1 0063209

(51) Int. Cl.
*G01N 33/487* (2006.01)
(52) U.S. Cl.
USPC .................. 204/403.01; 324/71.4; 73/61.71
(58) Field of Classification Search
USPC ................. 324/71.4, 71.1; 73/61.71; 377/12; 204/403.01, 400
See application file for complete search history.

(56) References Cited

U.S. PATENT DOCUMENTS

| | | | |
|---|---|---|---|
| 3,739,258 A * | 6/1973 | Karuhn et al. | 324/71.1 |
| 3,924,180 A * | 12/1975 | Salzman et al. | 324/71.1 |
| 4,760,328 A | 7/1988 | Groves | |
| 4,926,114 A | 5/1990 | Doutre | |
| 5,623,200 A * | 4/1997 | Ogino | 324/71.4 |
| 5,911,871 A | 6/1999 | Preiss et al. | |
| 6,111,398 A * | 8/2000 | Graham | 324/71.4 |
| 6,259,242 B1 | 7/2001 | Graham et al. | |
| 6,624,621 B2 | 9/2003 | North, Jr. | |
| 6,627,067 B1 * | 9/2003 | Branton et al. | 205/778 |
| 6,909,269 B2 * | 6/2005 | Nagai et al. | 324/71.4 |

OTHER PUBLICATIONS

Definition of align; Entry Printed from Oxford English Dictionary; Oxford University Press 2009.
Chinese Search Report for Chinese Application No. 200610063209.8.

\* cited by examiner

*Primary Examiner* — Luan Van
*Assistant Examiner* — Gurpreet Kaur
(74) *Attorney, Agent, or Firm* — Kory D. Christensen; Stoel Rives LLP

(57) ABSTRACT

The present invention discloses a device for detecting blood cells and a microscopic hole sensor assembly thereof. The device includes a microscopic hole sensor assembly positioned between a front pool and a back pool. The microscopic hole sensor assembly further includes a microscopic hole plate with a microscopic hole positioned thereon for communicating the front pool and the back pool. The end surface of the inlet is a flow-guiding surface gradually narrowing from the front pool to the back pool. The end surface of the outlet is a downstream surface gradually distending and extending towards the back pool. A straight effective orifice area is formed connecting the ends of the flow-guiding surface and the downstream surface.

20 Claims, 14 Drawing Sheets

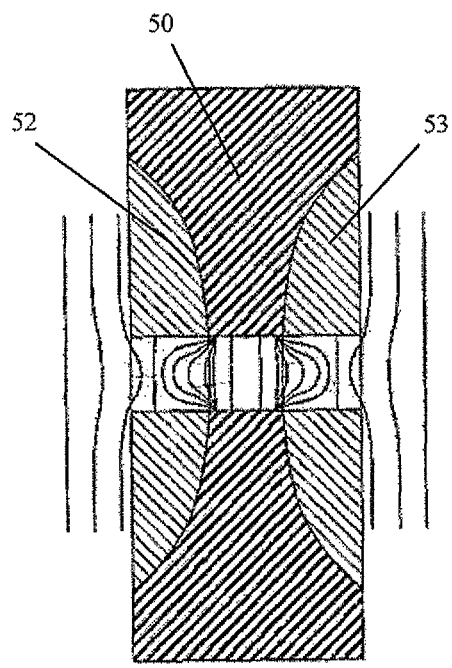
(a)
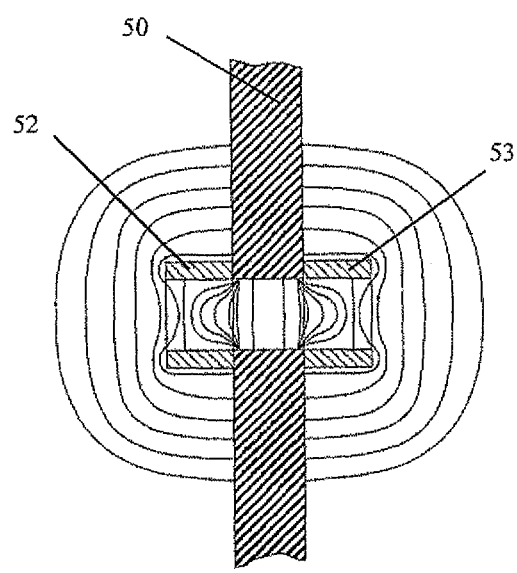
(b)
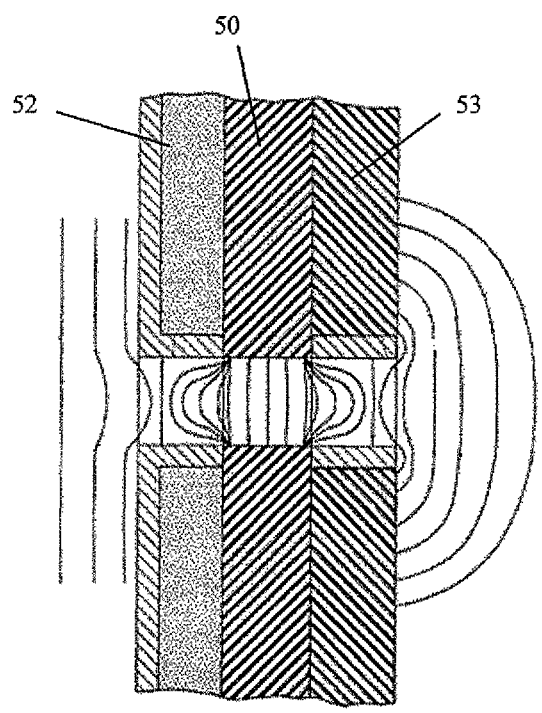
(c)
Fig. 4
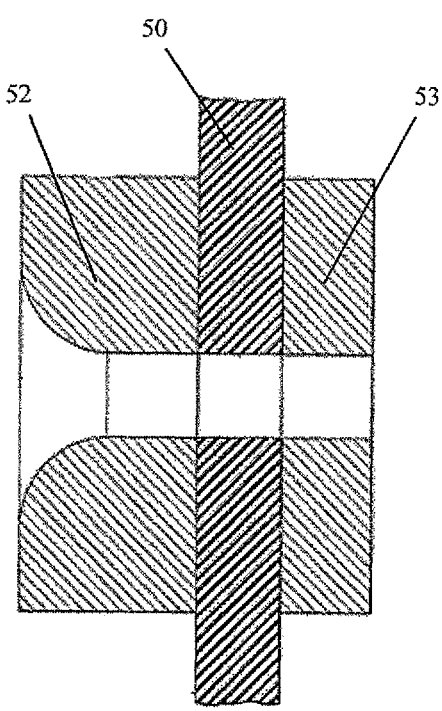
(d)

DEVICE FOR DETERMINATION OF PARAMETERS OF PARTICLES IN CONDUCTIVE SOLUTION AND MICROSCOPIC HOLE ASSEMBLY

CROSS-REFERENCE TO RELATED APPLICATION

The present invention claims the priority of China Application No. 200610063209.8, filed on Oct. 18, 2006, titled "DEVICE FOR DETECTING BLOOD CELLS AND MICROSCOPIC HOLE SENSOR ASSEMBLY THEREOF", which is filed by SHENZHEN MINDRAY BIO-MEDICAL ELECTRONICS, CO., LTD. The disclosure of the prior application is incorporated by reference herein in its entirety.

BACKGROUND OF THE INVENTION

1. Field of the Invention

The present invention relates to a device for determination of parameters of particles in conductive solution and, more particularly, to a device for measuring volumes of blood cells. The present invention also relates to a microscopic hole assembly used in the device.

2. Discussion of the Related Art

In conventional technologies of detecting and analyzing blood cells, an analysis of the blood cells is one of the most commonly conducted items in medical laboratories, which is useful for diagnosis as well as differentiate diagnosis of diseases, treatment and observation, retrospective analysis and analysis of heath condition.

At present, an impedance detection method using Coulter theory is one of the main methods used by a blood analyzer for sorting and counting. An absolute majority of three-classification blood cell analyzers used home and abroad takes advantage of the Coulter theory, also called, an impedance-based microscopic hole sensor blood cells counter, such as Sysmex KX-21, Coulter AC.T diff, Nihon Kohden MEK-516K, Horiba ABX Micros 60/CT, Mindray BC-3000Plus etc.

By Coulter theory refers to measurement of particles contained in a fluid according to different impedances resultant from different volumes of particles passing through a microscopic hole. Specifically, as blood cells pertain to a relatively poor conductor, they may change the original constant impedance both inside and outside the microscopic hole when the blood cells, suspended in a conductive solution, pass through the detection microscopic hole. Therefore, changes in the impedance are detectable by a sensor established in the microscopic hole and are processed by a processing circuit to generate electric pulses. Based on the amplitude of the pulse, the cell volume may be determined, and based on the number of the pulse, the cell number may also be determined. A directly perceivable distribution graph may be drawn to reflect the above electric-pulse signals, which is processed by a corresponding processing circuit. For example, when the blood analyzer is collecting various data of the erythrocytes, leucocytes and blood platelets, the volumes thereof (transverse axis) and relative occurrence frequencies (vertical axis) are shown as a curve graph in a coordinate system, thus forming a histogram showing the blood cell distribution.

Referring to FIG. 1a, a conventional microscopic hole sensor and its equipotential lines are schematically shown. In FIG. 1a, four tracking paths PI, PII, PIII, PIV and three refluent paths RI, RII, RIII of the particles are exemplified. FIG. 1b shows a waveform diagram of the pulses generated by individual paths of the particles as shown in FIG. 1a. As can be seen from FIG. 1b, the closer the particles come to the wall of the microscopic hole, the greater disturbance occurs to the measured signals thereof. For example, the particles in the tracking path PIV generate an obvious M-shaped waveform signal, and those in the tracking path PI are given the most accurate measurement. Though a slight change happens to the measured signals of the particle in the tracking paths PII, PIII, it does not lead to a serious distortion. FIG. 1c shows signals in small fat form generated by the different paths of individual refluent particles shown in FIG. 1a. As apparent from FIG. 1c, the particles in the path RIII generate rather huge fat signals, as compared with the best-measured signals of the particles in the tracking path PI. The fat signals generated by the particles in the path RIII may adversely affect the measurement result. FIG. 1d shows an inaccurate histogram of detected particles caused by the anomalous paths and refluences. For example, the accumulated effect produced by the anomalous paths of the particles in path PIV and the refluences of the particles in the refluent path RIII leads to an accumulated distortion in the histogram of FIG. 1d. The shadowy portion in FIG. 1d represents an accumulated distortion. Therefore, the measurement result suffers from a serious distortion.

In current blood-cell analyzers, most of the counting microscopic hole sensors adopt a system structure shown in FIG. 3 and arrange the microscopic hole sensor between two liquid pools 110 and 120. Through adjusting pressures of the two liquid pools 110 and 120, e.g., applying a positive pressure to the liquid pool 110 and meanwhile applying a negative pressure to the liquid pool 120, the liquid may be measured based on the Coulter theory when the liquid is driven to flow through the microscopic hole sensor of the microscopic hole sensor assembly structure 100.

However, in the structure of the conventional microscopic hole sensor assemblies, the wall surface of the microscopic hole sensor at each liquid pool side is perpendicular to the orifice path 130 defined in the microscopic hole sensor. Consequently, due to the collecting effect of the liquid, when passing the microscopic hole sensor assembly, the liquid carrying particles may rush into the orifice path 130 or adhere to the wall surface of the orifice path 130. Therefore, unfavorable effect is produced to the measurement, such as the anomalous paths shown in FIG. 1b and the refluence shown in FIG. 1c.

Normally, prior art counting signal of the blood cells have faults shown in FIGS. 2a to 2d, to be more specific, slow signal rise edges and steep signal fall edges shown in FIGS. 2a and 2b, undue M-shaped waves and multi-peak waves of signals shown in FIG. 2c, and undue unknown signals and serious noises shown in FIG. 2d. Therefore, U.S. Pat. No. 6,111,398 discloses a microscopic hole sensor assembly for detecting particles, which has the four configurations as shown in FIGS. 4(a) to 4(d). The assembly concerned is mainly consisting of an insulated slice 50 (made of an insulated material, such as gem, ceramic or glass) and conductive slices 52, 53 (made of metal, conductive ceramic, etc.) arranged at two sides of the insulating slice 50. The US patent also discloses features of a microscopic hole detecting device, structure and size of a microscopic hole, material of the microscopic hole, drive circuit, and so on.

The Coulter-based microscopic hole sensor assembly disclosed in the above US patent partially solves the above-mentioned problems to some extent. For example, the embodiments shown in FIGS. 4(a) to 4(d) offer an excellent solution to the cell refluence and the M-shaped wave generated by the anomalous paths. However, the introduction of rather thick fore-and-aft conductive materials 52, 53 into the Coulter microscopic hole sensor assembly increases the effective deepness of the orifice. In this way, some protein and cell fragments in the blood can easily adhere to the circumference of the microscopic hole. Consequently, in addition to an unfavorable effect on the signal quality of the cell counting pulse, a jam phenomenon may easily occur in the counting process. Therefore, the Coulter-based blood cell analyzer adopts additional expensive equipment for obviating the jam.

In a word, some conventional technologies fail to eliminate aberrance and noise of the detection signals. To solve this problem, some technologies as disclosed propose to establish conductive materials, which however have a rather strict demand on the configuration of the microscopic hole assembly. In addition, a new problem has arisen, i.e., the above jam phenomenon. As such, expensive equipment for obviating the jam must be additionally introduced therein, which enhances the production cost of the device.

Therefore, an earnest need exists to improve and develop the prior art technologies.

SUMMARY OF THE INVENTION

An object of the present invention is to provide a device for determination of parameters of particles in a conductive solution and a microscopic hole sensor assembly thereof. This device eliminates slow rise edge and steep fall edge of the blood cell signals, obvious M-shaped wave of the signals and unknown signals such as multi-peak waves, improves the signal-to-noise ratio. Furthermore, the device restrains refluence of the blood cells in the liquid pool, having passed through the counting microscopic hole, so that the flow field characteristic of the particles when passing through the sensor microscopic hole are improved and the orifice path is clear from jam.

According to an aspect of the present invention, the present invention provides a device for determination of parameters of particles in a conductive solution. The device includes a front pool, a back pool spaced from the front pool, and a microscopic hole sensor assembly. The microscopic hole sensor assembly includes a microscopic hole plate with a microscopic hole defined therein, electrodes respectively arranged in the front pool and the back pool, and a processing circuit connecting the electrodes in the front pool and the back pool. The microscopic hole includes an inlet and an outlet and communicates the front pool with the back pool. The electrodes are configured for forming an electric current between the front pool and the back pool via the conductive solution passing through the microscopic hole. The processing circuit is configured for detecting the electric current and/or changes of an electric field of the electric current, and outputs a detection result. An end-surface of the inlet is a flow-guiding surface gradually narrowing from the front pool towards the back pool, and an end-surface of the outlet is a downstream surface gradually distending and extending towards the back pool, so as to form an effective orifice area configured for determining the parameters of the particles in the microscopic hole.

In an embodiment, the microscopic hole sensor assembly further includes a flow-guiding plate positioned at an end surface of the inlet. The flow-guiding surface is formed by a front end surface of the flow-guiding plate, and a rear end surface of the flow-guiding plate and a front end surface of the microscopic hole plate are matchingly assembled to form an effective orifice area configured for accelerating liquid flow at a corresponding position within the microscopic hole. The flow-guiding plate can be a good electric conductor and can be configured to comprise the electrode in the front pool.

In another embodiment, the microscopic hole sensor assembly further includes a fixed seat positioned at the end surface of the outlet. The fixed seat comprises the downstream surface gradually distending and extending towards the back pool.

Alternatively, the back pool is configured to be a sealed pool. A negative pressure extracting outlet and the electrode therein are outwardly positioned and aligned with the microscopic hole. At least one inlet is positioned along the downstream surface for washing the back pool.

In addition, a thickness of the effective orifice area of the microscopic hole plate is 1.1 to 4 times of that of the flow-guiding plate.

Further, each of the flow-guiding surface and the downstream surface can be configured to comprise a bugle-shaped, circular, convex, conical, or concave whirly curved surface.

According to another aspect of the present invention, the present invention realizes the above object by providing a microscopic hole sensor assembly used in a device for determination of parameters of particles. The device includes a front pool and a back pool spaced from each other. The microscopic hole sensor assembly is positioned between the front pool and the back pool. The microscopic hole sensor assembly includes a microscopic hole plate with a microscopic hole defined therein, electrodes respectively arranged in the front pool and the back pool, and a processing circuit connecting the electrodes in the front pool and the back pool. The microscopic hole includes an inlet and an outlet and communicates the front pool with the back pool. The electrodes are configured for forming an electric current between the front pool and the back pool via a conductive solution passing through the microscopic hole. The processing circuit is configured for detecting the electric current and/or changes of an electric field of the electric current, and outputs a detection result. An end-surface of the inlet is a flow-guiding surface gradually narrowing from the front pool to the back pool, so as to form an effective orifice area configured for determining the parameters of the particles in the microscopic hole.

In an embodiment, an end-surface of the outlet is a downstream surface gradually distending and extending towards the back pool.

In another embodiment, the microscopic hole sensor assembly further includes a flow-guiding plate positioned at an end surface of the inlet. The flow-guiding surface is formed by a front end surface of the flow-guiding plate. A rear end surface of the flow-guiding plate and a front end surface of the microscopic hole plate are matchingly assembled to form an effective orifice area configured for accelerating liquid flow at a corresponding position within the microscopic hole. The flow-guiding plate can be a good electric conductor and can be configured to comprise the electrode in the front pool.

Alternatively, the microscopic hole sensor assembly further includes a fixed seat positioned at the end surface of the outlet. The fixed seat comprises the downstream surface gradually distending and extending outwardly from the end surface of the outlet. Each of the flow-guiding surface and the downstream surface can be configured to comprise a bugle-shaped, circular, convex, conical, or concave whirly curved surface.

According to still another aspect of the present invention, the present invention realizes the above object by providing a microscopic hole sensor assembly used in a device for determination of parameters of particles. The device includes a front pool and a back pool spaced from each other. The microscopic hole sensor assembly is positioned between the front pool and the back pool. The microscopic hole sensor assembly includes a microscopic hole plate with a microscopic hole defined therein, electrodes respectively arranged in the front pool and the back pool, and a processing circuit connecting the electrodes in the front pool and the back pool. The microscopic hole includes an inlet and an outlet and communicates the front pool with the back pool. The electrodes are configured for forming an electric current between the front pool and the back pool via a conductive solution passing through the microscopic hole. The processing circuit is configured for detecting the electric current and/or changes of the electric field of the electric current, and outputs a detection result. An end-surface of the outlet is a downstream surface gradually distending and extending backwards, so as to form an effective orifice area configured for detection in the microscopic hole.

In an embodiment, the microscopic hole sensor assembly further includes a fixed seat positioned at the end surface of the outlet. The fixed seat comprises the downstream surface gradually distending and extending outwardly from the end surface of the outlet.

In another embodiment, the downstream surface can be configured to comprise a bugle-shaped, circular, convex, conical, or concave whirly curved surface.

Alternatively, the electrode in the back pool is positioned on the fixed seat.

Since an improved microscopic hole orifice path structure is adopted by the present device and the microscopic hole sensor assembly thereof, the blood cells in the fluid to be measured flow collectively towards the center of the orifice path. Further, the adopted expansile outlet reduces the refluence, which improves the flow field characteristic of the blood cell particles when passing through the sensor microscopic hole, reduces interference to the measured signals, and thereby enhances the quality of the blood cell counting signal as well as eliminates the possibility in blocking the microscopic hole orifice path. In addition, the device according to the present invention is simple, and production cost thereof is thus reduced.

Other and further objects of the invention will be apparent from the following drawings and description of preferred embodiments of the invention in which like reference numerals are used to indicate like parts in the various views.

BRIEF DESCRIPTION OF THE DRAWINGS

Many aspects of the present invention can be better understood with reference to the following drawings. The components in the drawings are not necessarily drawn to scale, the emphasis instead being placed upon clearly illustrating the principles of the present invention. Moreover, in the drawings, like reference numerals designate corresponding parts throughout the several views.

FIGS. 1a to 1d show the measuring theory of a conventional Coulter-based microscopic hole blood analyzer, wherein FIG. 1a shows a distribution of equipotential lines in the orifice path of a conventional counting microscopic hole; FIG. 1b shows pulse waveforms generated by particles in different paths as shown in FIG. 1a; FIG. 1c shows small fat signals caused by refluence of the refluent particles in different paths in FIG. 1a; and FIG. 1d shows a measurement result histogram with an accumulated part caused by the faulty particles in FIG. 1a;

FIGS. 2a to 2d show familiar defective measurement results using a conventional Coulter-based microscopic hole sensor, wherein FIG. 2a shows a pulse diagram with a slow rise edge of a signal; FIG. 2b shows a pulse diagram with a steep fall edge of a signal; FIG. 2c shows a signal with undue M-shaped waves (eight M-shaped waves are shown) and multi-peak waves, and FIG. 2d shows a signal with undue unknown signals and serious noises;

FIGS. 4(a) to (d) are schematic, structural illustrations of four conventional Coulter-based microscopic hole sensors;

FIG. 7b is a diagram showing the speed distribution of particles in the orifice path of the microscopic hole of the assembly of FIG. 7a;

FIG. 7c shows a processed signal diagram of the microscopic hole sensor assembly of FIG. 7a;

FIG. 8a is a schematic illustration of a flow field of a conventional Coulter-based microscopic hole sensor assembly, while FIGS. 8b and 8c are schematic illustrations of the flow field of the microscopic hole sensor assembly according to the embodiment of the present invention;

FIG. 10a is a diagram showing volumes of the blood cells using a conventional measuring technique, while

DESCRIPTION OF THE PREFERRED EMBODIMENTS

Reference will now be made to the figures to describe the present invention in detail.

Figure 1A:
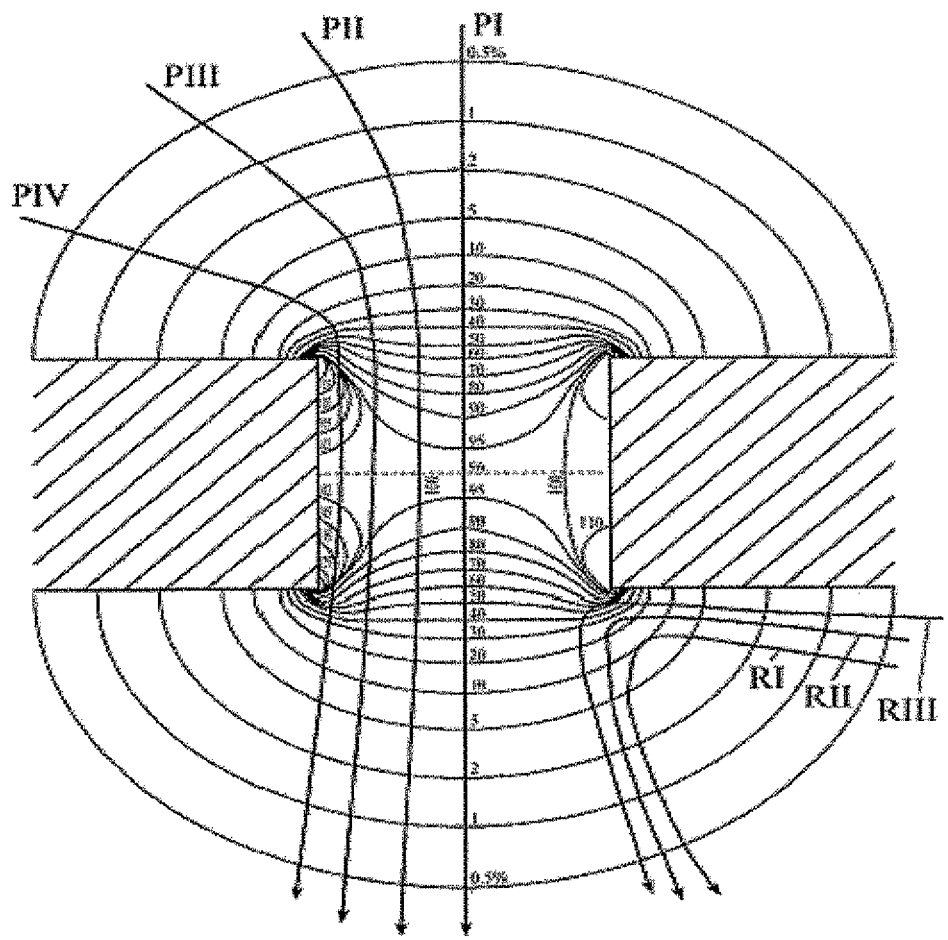
Figure 1B:
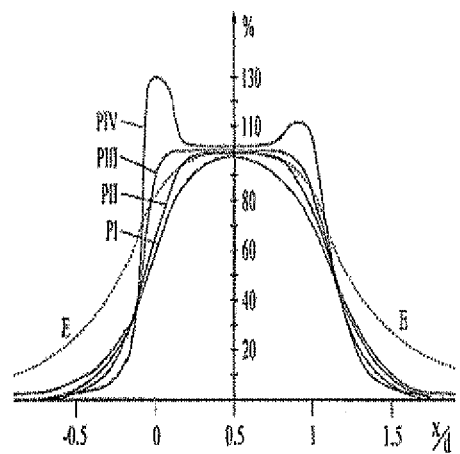
Figure 1C:
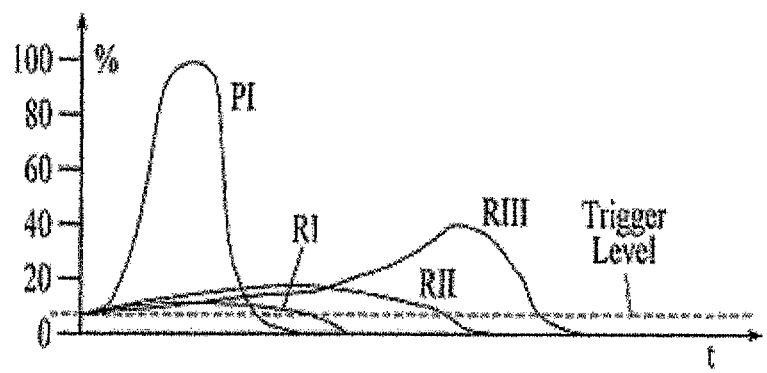
Figure 1D:
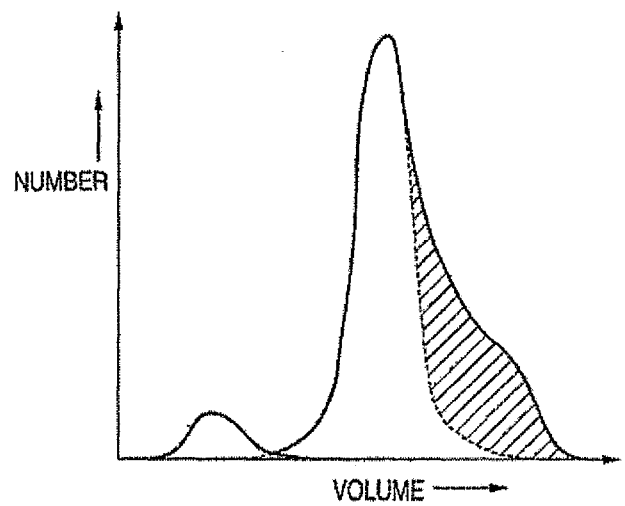
Figure 2A:
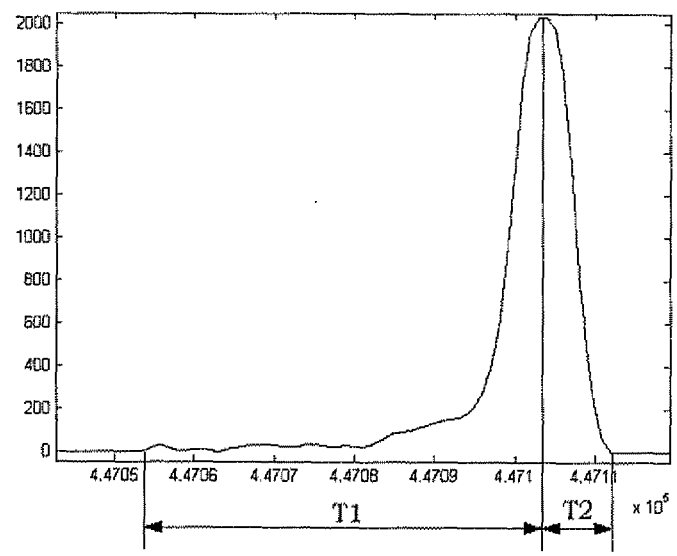
Figure 2B:
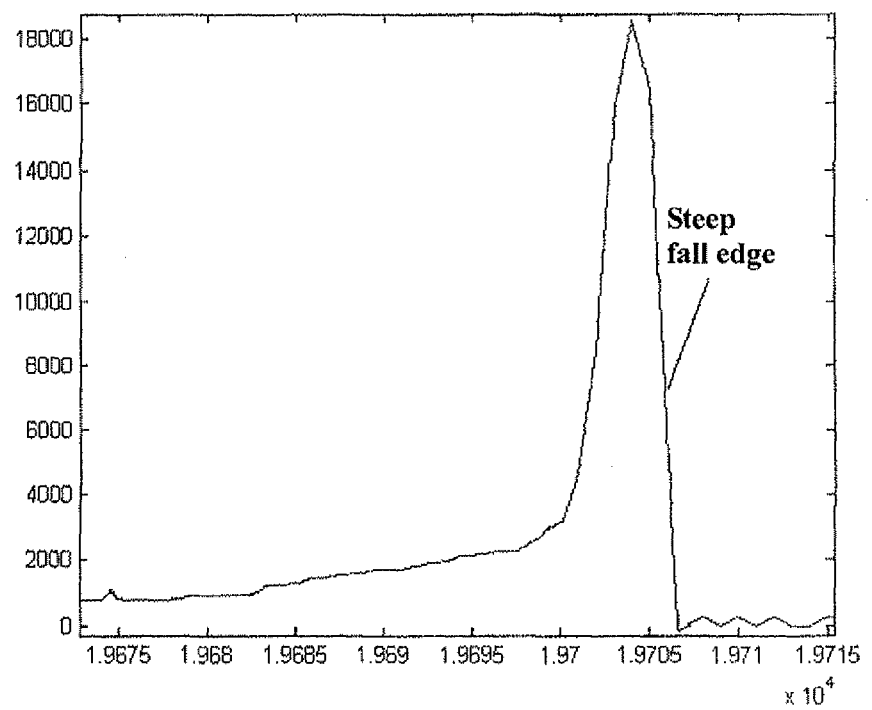
Figure 2C:
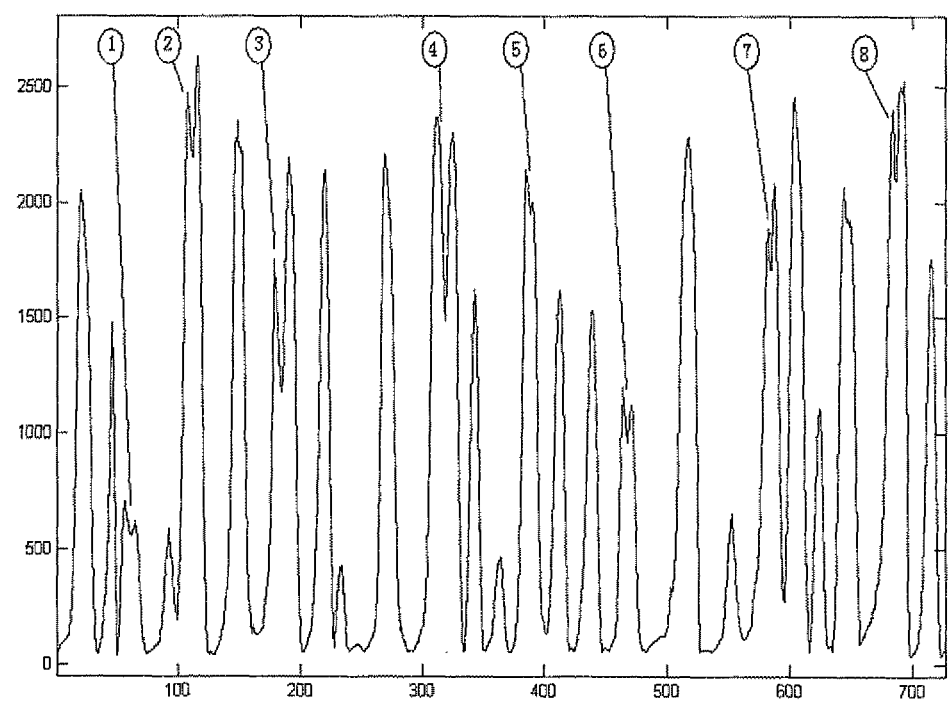
Figure 2D:
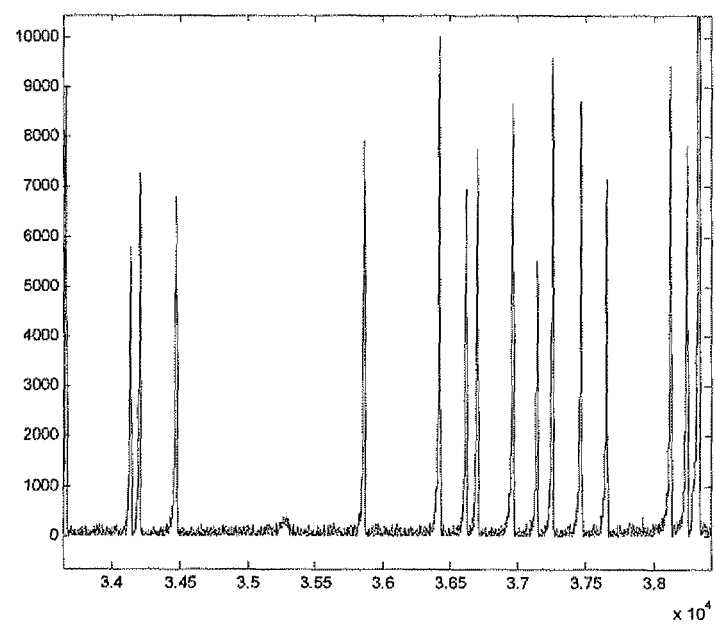
Figure 3:
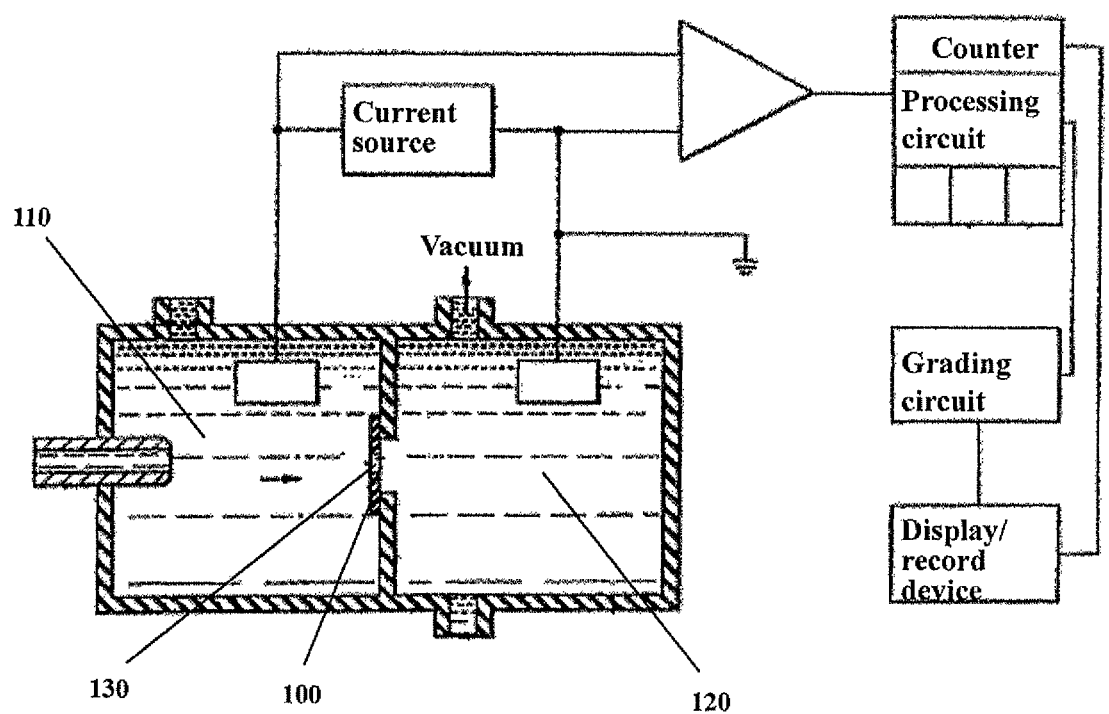
FIG. 3 is a schematic, structural illustration of a conventional device for measuring volumes of blood cells.
Figure 5:
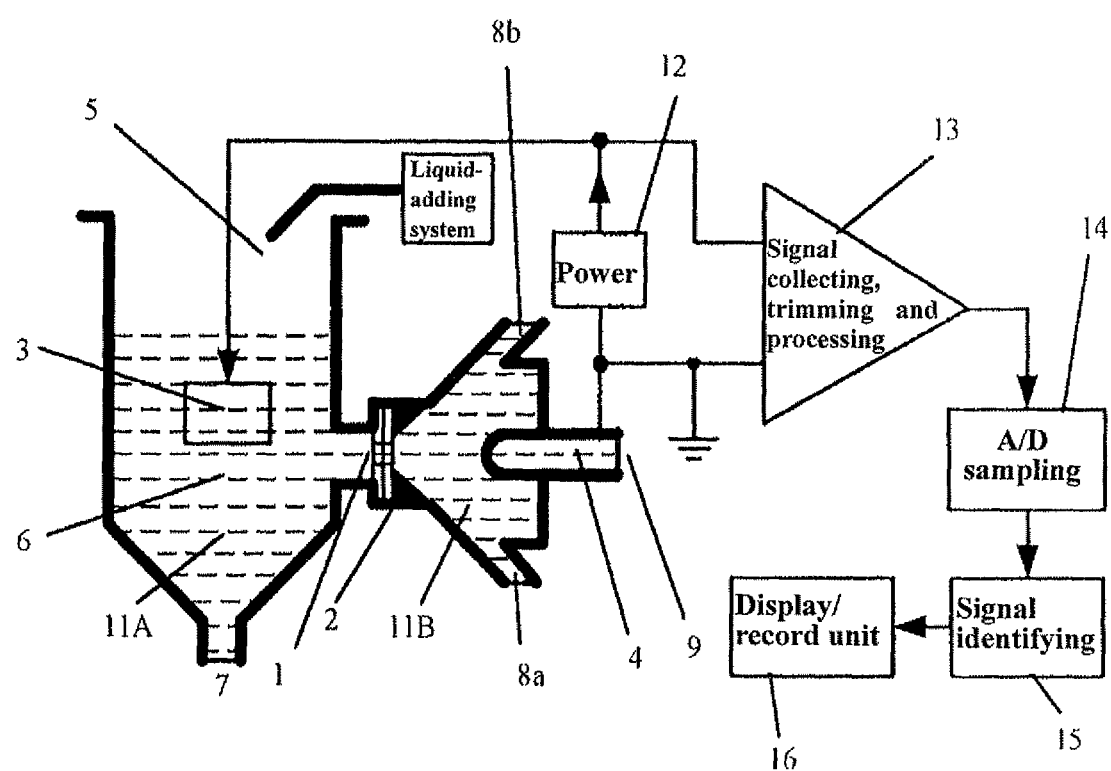
FIG. 5 is a schematic, structural illustration of the device for measuring volumes of blood cells according to an embodiment of the present invention.
Figure 6:
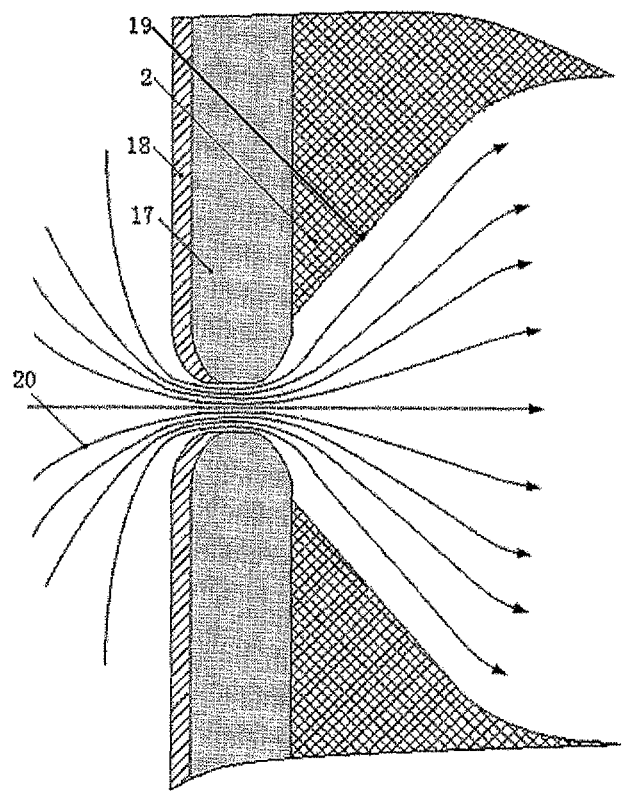
FIG. 6 is a schematic, structural illustration of the microscopic hole assembly and the fixed seat thereof according to an embodiment of the present invention.

The present device for detecting blood cells or other non-conductive particles based on Coulter theory is shown in FIG. 5, which is a block diagram showing the working principles of the detection and counting device. The device includes a microscopic hole sensor assembly 1, a front pool 11A located in front of the microscopic hole assembly 1, and a back pool 11B located behind the microscopic hole assembly 1. The front pool 11A and the back pool 11B are connected via a microscopic hole defined in the microscopic hole assembly 1. Referring to FIG. 6, the back pool 11B has a bugle-shaped distended downstream surface 19. The bottom of the downstream surface 19 is secured to a fixed seat 2.

A platinum anode electrode 3 is arranged in the front pool 11A, and a cathode electrode 4 is arranged in the back pool 11B. An inlet 5 of a liquid-adding system is mounted above the front pool 11A to add a solution 6 with blood cells suspended therein in the front pool 11A. The bottom of the front pool 11A is provided with an opening 7 for discharging the liquid from the front pool 11A after measurement, and for pumping air bubbles therein during the detection process to keep the solution suspended for the convenience of detection.

The solution 6 with blood cells suspended therein flows to the back pool 11B through the microscopic hole assembly 1. Inlets 8a and 8b are arranged in the back pool 11B for washing the back pool 11B. Preferably, the two inlets 8a and 8b are arranged along the distended downstream surface 19. By such a configuration, the washing liquid is introduced in against the outflow direction of the solution, so that the back pool 11B can be quickly and effectively washed.

The back pool 11B is configured to be a sealed pool, and a negative pressure extracting outlet 9 is arranged therein so that the solution can flow from the front pool 11A to the back pool 11B. The anode electrode 3 in the front pool 11A and the cathode electrode 4 in the back pool 11B are capable of detecting an impedance change of the cell particles in the solution. Actually, the sensor electrodes, i.e., the anode electrode 3 and the cathode electrode 4, can be arranged closely before and behind the microscopic hole assembly 1. Preferably, the sensor electrodes are arranged close to the microscopic hole plate 17, and the line connecting these electrodes is centered in the microscopic hole of the microscopic hole plate 17. Thus, the sensor electrodes can form a constant current through the solution 6. The configuration of the microscopic hole in the microscopic hole plate 17 helps to maintain a stable impedance during the constant electrical conduction. When particles with a poor conductivity, such as a blood cell, passe through the microscopic hole in the microscopic hole plate 17, the impedance of the microscopic hole sensor changes. Subsequently, the sensor electrodes detect a voltage pulse and output it to an outer processing circuit. The sensor electrodes arranged close to the microscopic hole plate 17 can decrease interference signals.

The microscopic hole in the present microscopic hole plate 17 has a rather small dimension up to tens of microns, and therefore the sensor electrodes can be arranged close to the microscopic hole plate, as shown in FIG. 6 The flow-guiding plate 18 can be configured to comprise the anode electrode 3, and the cathode electrode can be arranged on the surface of the fixed seat 2.

The circuit configured within the present detection device further includes a current source driving unit 12 used for driving the sensor electrodes (i.e., the anode electrode 3 and the cathode electrode 4) to detect the impedance change and outputting an detected signal. The circuit also includes a signal collecting, trimming and processing unit 13 useful for trimming the detected signal, which is then processed by a signal A/D sampling unit 14 and a signal arithmetic identifying and processing unit 15 and finally displayed on a recording unit 16. As shown in FIG. 5, the arrows indicate the flowing direction of the current or the signals. The processing of the circuit is well known in the art and thereby is not described in detail herein.

The present device also provides a microscopic hole assembly 1. As shown in FIG. 6, the end surface of the outlet thereof is provided with a bugle-shaped downstream surface 19 gradually distending towards the back pool. The downstream surface 19 is useful for reducing the liquid speed at the outlet of the microscopic hole and preventing refluence, so as to reduce steep fall edges and interference to the signals. The downstream surface 19 has its bottom secured to a fixed seat 2. The microscopic hole assembly 1 includes a microscopic hole plate 17, a flow-guiding plate 18, and the fixed seat 2. The microscopic hole plate 17 defines a microscopic hole therein. Inside the microscopic hole has a certain straight area defined as an effective orifice area. The end surface edge of the inlet of the microscopic hole is configured to comprise a whirly curved surface, thereby forming a flow-guiding surface gradually narrowing from the front pool towards the back pool. The flow-guiding surface may take the form of a flow-guiding plate 18 arranged along the curved end of the inlet of the microscopic hole. The fixed seat 2 is mounted to the outlet of the microscopic hole and is connected to the bugle-shaped downstream surface 19. Thus, when the solution is passing through the microscopic hole plate 17, a constant speed and smooth flow field is obtained within the effective area in the microscopic hole. An effective orifice area is also defined on the flow-guiding plate 18 at a position corresponding to the microscopic hole in order for accelerating the liquid flow. The front flow-guiding surface of the flow-guiding plate 18 is configured for focusing and smoothing the liquid flow so that the slow front edge and quality of the signal can be improved and enhanced.

It should be noted that the present microscopic hole plate 17 can be configured to comprise a flow-guiding surface at the front and a downstream surface at the back, without the flow-guiding plate 18. Thus, the structures of the components are simplified, which facilitates the production. In addition, based on the technical solutions of the present invention, those skilled in the art can determine when to reserve the flow-guiding surface but abandon the downstream surface, or vise versa, as desired. Though the signal quality may not be optimum under these situations, it is still acceptable so long as the front edge or the rear edge of the signal satisfies relevant requirements. Thus, manufacture of the device may be less complicated, and thereby the device cost is decreased and meanwhile actual requirements are satisfied.

In case of an ideal microscopic hole sensor, the cells move from the inlet to the outlet at a constant speed and generate an ideal voltage waveform. The waveform should present equal rise edge and fall edge and a bilateral symmetry (i.e., T1=T2). However, in actual operation of a conventional sensor, as the microscopic hole therein produces a collecting effect, the liquid flow thereby may accelerate into the microscopic hole. Therefore, the liquid speed at the microscopic hole inlet is slow, and reaches to the top within the microscopic hole, thereby generating a pulse signal with a relative slow front edge (T1>T2). The main reason therefor is as follows: the speed of the cell flowing into the microscopic hole sensitivity area is slowly increased, which prolongs the time for the cell to move from the microscopic hole weak sensitivity area to the strongest sensitivity area, and thereby the slow front edge of the cell signal is caused. The slow front edge increases the probability of signal superposition, and adversely affects the accuracy in identifying the signal amplitude.

Figure 7A:
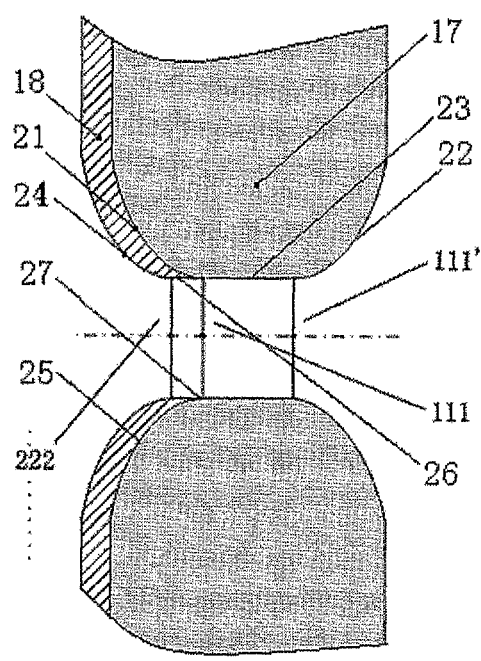
FIG. 7a is a schematic, structural illustration showing the working principles of the microscopic hole assembly of FIG. 6.

The present microscopic hole sensor assembly is shown in FIG. 7a. A flow-guiding plate 18 is provided at the front end of the microscopic hole plate 17, which plate has a smooth bugle-shaped front end curved surface 21 (or different shapes of curved surface). The flow-guiding plate 18 improves the distribution of the electric field at the inlet of the microscopic hole sensor and restricts the electric field sensitivity area to the neighborhood of the sensor microscopic hole inlet area. Under the negative pressure applied to the back pool, the solution with sample blood cells suspended therein starts to flow through the microscopic hole sensor assembly, and then is focused and quickly accelerated under the action of the flow-guiding plate 18. Thus, the flowing speed of the sample liquid flowing into the microscopic hole rises in no time, that is, the cells accelerate at the microscopic hole inlet. In contrast, the speeds at the inlet 111 and the outlet 111' of the microscopic hole sensor remain substantially the same.

Figure 7B:
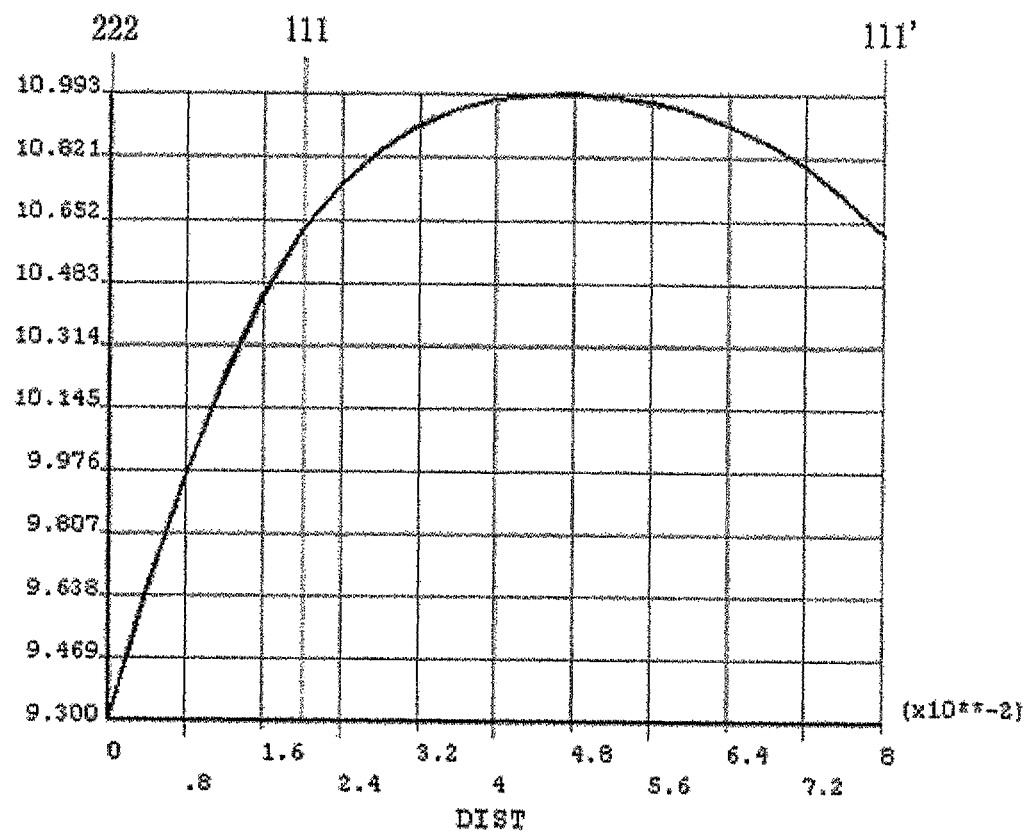

Referring to FIG. 7b, the speed at the inlet 111 of the present microscopic hole sensor and the speed at the outlet 111' thereof are substantially the same, so that the cells move at the same or approximate speed at both the inlet and outlet of the microscopic hole. Consequently, the slow-risen front edge of the blood cell signal is improved.

Figure 7C:
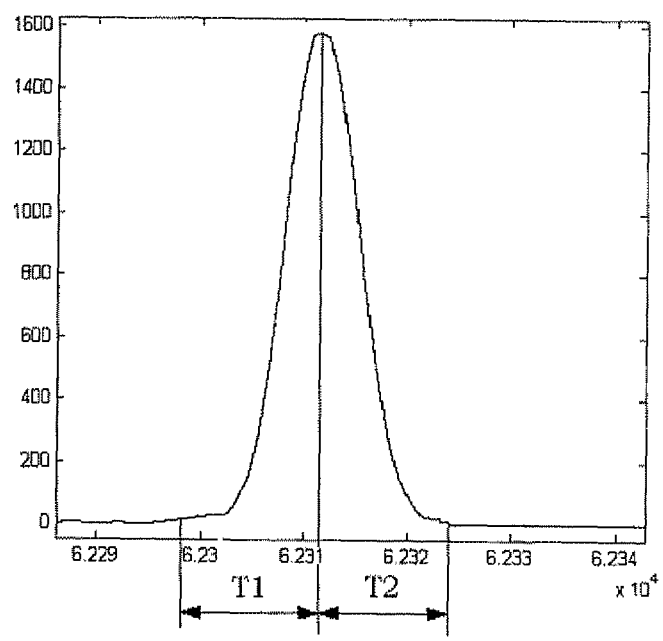

In addition, the present flow-guiding plate of the present invention also improves the anomalous path at the inlet of the microscopic hole, so that most cells pass through the microscopic hole in a direction parallel to the central axis of the microscopic hole in the microscopic hole plate 17 and close to the central axis as well. Thus, the probability in generating an M-shaped wave is reduced, and the signal-to-noise ratio of the signal is enhanced, as is shown in FIG. 7*c*.

Figures 8A, 8B, 8C:
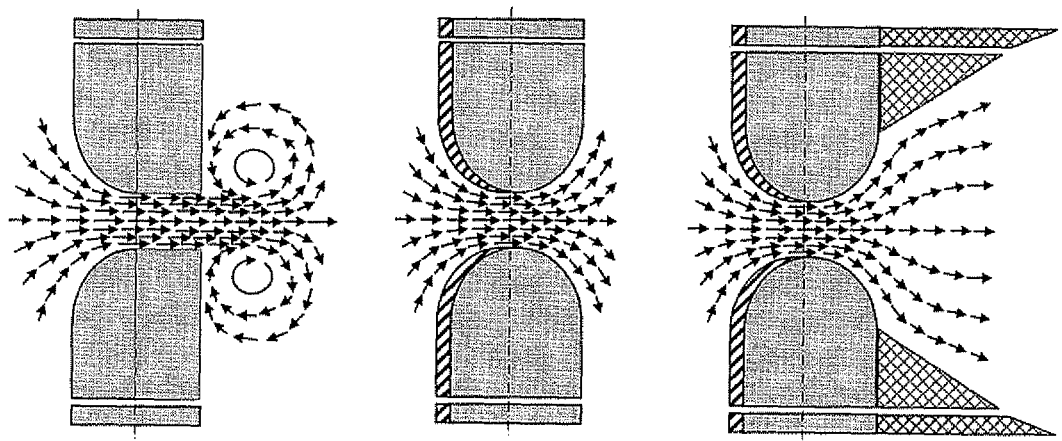

Referring to FIG. 7*a*, the rear end surface 22 of the outlet in the present microscopic hole plate 17 utilizes a bugle-shaped downstream surface gradually distending towards the back pool direction. Specifically, the downstream surface can be arranged to be a curved surface (or different shapes of curved surface). FIG. 8*a*, FIG. 8*b* and FIG. 8*c* show a combination of flow fields between a microscopic hole sensor assembly with a bugle-shaped downstream surface at the outlet and an assembly without such a surface. FIG. 8*a* shows the absence of such a downstream surface. As seen therefrom, either side of the microscopic hole outlet has refluence, which can affect the signal detection. FIG. 8*b* shows the presence of a bugle-shaped and whirly curved surface. The flow field characteristics are apparent from the figure, and obviously the refluence effect is removed. More preferably, as shown in FIG. 8*c*, a fixed seat is established to comprise a bugle-shaped distended downstream surface. In this case, the flow field is promised to be more stable. The flow field in the microscopic hole is maintained uniform and smooth, so that the sample liquid passing through the microscopic hole sensor assembly forms a stable liquid flow line. Analyses of experiments indicate that the microscopic hole sensor assembly of the present invention effectively improves the slow front edge of the counting signal, reduces the probability in generating the M-shaped wave and enhances the signal-to-noise ratio. Thus, the accuracy of the blood analyses is effectively enhanced. Further, the present microscopic hole sensor has a fairly simple structure and thus could be easily produced. Furthermore, the microscopic hole would not be blocked.

In view of the manufacture process, the design of the microscopic hole sensor assembly of the present invention may be, but not limited to, those several structures shown in FIGS. 9*a* to 9*j*. The front end surface 21 of the microscopic hole plate 17 can be configured as a bugle-shaped, circular, convex, conical, concave and whirly curved surface, or right-angle plane. The rear end surface 22 of the microscopic hole plate can be configured as a bugle-shaped, circular, convex, or conical and whirly curved surface. The front end surface 24 of the flow-guiding plate 18 can be configured as a bugle-shaped, circular, convex, conical, or concave whirly curved surface. The rear end surface 25 of the flow-guiding plate fit in shape with the front end surface 21 of the microscopic hole plate 17.

Referring to FIG. 9*a*, the front end surface of the microscopic hole plate 17 is a straight plane, while the rear end surface thereof is a conical whirly curved surface; the front end of the flow-guiding plate 18 is a convex whirly curved surface, and the rear end surface thereof is a straight plane fitting with the front end surface of the microscopic hole plate 17. Referring to FIG. 9*b*, both the front end surface and the rear end surface of the microscopic hole plate 17 are conical whirly surface; the front end of the flow-guiding plate 18 is a convex whirly curved surface, and the rear end surface thereof is a conical whirly curved surface fitting with the front end surface of the microscopic hole plate 17. Referring to FIG. 9*c*, both the front end surface and the rear end surface of the microscopic hole plate 17 are conical whirly surface; the front end of the flow-guiding plate 18 is conical whirly curved surface, and the rear end surface thereof is a conical whirly surface fitting with the front end surface of the microscopic hole plate 17. Referring to FIG. 9*d*, the front end surface of the microscopic hole plate 17 is a straight plane, the rear end surface thereof is a conical whirly surface; the front end of the flow-guiding plate 18 is concave whiny curved surface, and the rear end surface thereof is a straight plane fitting with the front end surface of the microscopic hole plate 17. Referring to FIG. 9*e*, the front end surface of the microscopic hole plate 17 is bugle-shaped, the rear end surface thereof is a combination consisting of a conical whirly curved surface at the front section and a bugle-shaped whirly curved surface at the rear section; the front end of the flow-guiding plate 18 is bugle-shaped, the rear end surface thereof is a bugle-shaped surface fitting with the front end surface of the microscopic hole plate 17. Moreover, the thickness of the flow-guiding plate is uniform in order to fit with the front end surface of the microscopic hole sensor. Referring to FIG. 9*f*, the front end surface of the microscopic hole plate 17 is a straight plane, the rear end surface thereof is a convex whirly curved surface; the front end of the flow-guiding plate 18 is a convex whirly curved surface, and the rear end surface thereof is a straight plane fitting with the front end surface of the microscopic hole plate 17. Referring to FIG. 9*g*, the front end surface of the microscopic hole plate 17 is a conical whirly surface, the rear end surface is a convex whirly curved surface; the front end of the flow-guiding plate 18 is a convex whirly curved surface, and the rear end surface thereof is a conical whirly curved surface fitting with the front end surface of the microscopic hole plate 17. Referring to FIG. 9*h*, the front end surface of the microscopic hole plate 17 is a straight plane, the rear end surface thereof is a convex whirly curved surface; the front end surface of the flow-guiding plate 18 is a conical whirly curved surface, and the rear end surface thereof is a straight plane fitting with the front end surface of the microscopic hole plate 17. Referring to FIG. 9*i*, the front end surface of the microscopic hole plate 17 is a straight plane, the rear end surface thereof is a convex whirly curved surface; the front end of the flow-guiding plate 18 is a concave whirly curved surface, and the rear end surface thereof is a straight plane fitting with the front end surface of the microscopic hole plate 17. Referring to FIG. 9*j*, the front end surface of the microscopic hole plate 17 is a concave whirly surface, the rear end surface thereof is a convex whirly curved surface; the front end of the flow-guiding plate 18 is a concave whirly curved surface. Moreover, the whole flow-guiding plate is uniform in thickness, and the rear end surface thereof is a convex whirly curved surface fitting with the front end surface of the microscopic hole plate 17.

The materials for the microscopic hole plate 17 are similar to those for the known structures, i.e., an insulating material such as gem, ceramic, latent semiconductor, glass etc. The material should satisfy good thermal stability, and should be suitable for mechanical processing. Further, the material should exhibit a small thermal expansion coefficient, and excellent abradability, acid/alkaline resistance and rust resistance, as well as certain stiffness and rigidity. The end surface of the microscopic hole plate should be smooth enough to closely and securely adhere to the front flow-guiding plate 18. The opening of the microscopic hole distends gradually so as to form a bugle-shaped or convex curved rear end surface 22 which presents good flow field characteristic. In this way, the liquid exiting from the outlet slowly diffuse around to reduce and prevent liquid refluence.

The material for the flow-guiding plate 18 should be a good electric conductor. The flow-guiding plate can act as an anode and should not be electrolyzed in a conductive solution subjected to a high DC voltage. Consequently, the material thereof may be selected from the platinum-group metal such as gold, nickel, titanium etc., or alloys of platinum-group metal. The material for the flow-guiding plate should satisfy good thermal stability, and should be suitable for mechanical processing. Further, the material should an excellent abradability, acid/alkaline resistance, and rust resistance. Besides, the material for the plate should have a thermal expansion coefficient extremely close to that for the microscopic hole plate, in order that they would not disengage in case of change in environment temperature and closely and securely connect with each other. The flow-guiding plate has following functions of: improving characteristic of electric field distribution and the flow field at the inlet of the sensor microscopic hole, eliminating the anomalous path when the cells enter the microscopic hole, restraining the cells from entering into the orifice area close to the edge of the microscopic hole, and enhancing the speed of the particles when entering into the sensitivity area of the microscopic hole.

The fixed seat 2 may be made of insulating materials such as macromolecule organic plastic. These materials should satisfy good thermal stability, abradability, strong acid/alkaline resistance, and rust resistance.

The thickness of the effective orifice area of the microscopic hole plate should be 1.1 to 4 times of that of the flow-guiding plate in order to ensure the accuracy of the measured signal.

Figure 9:
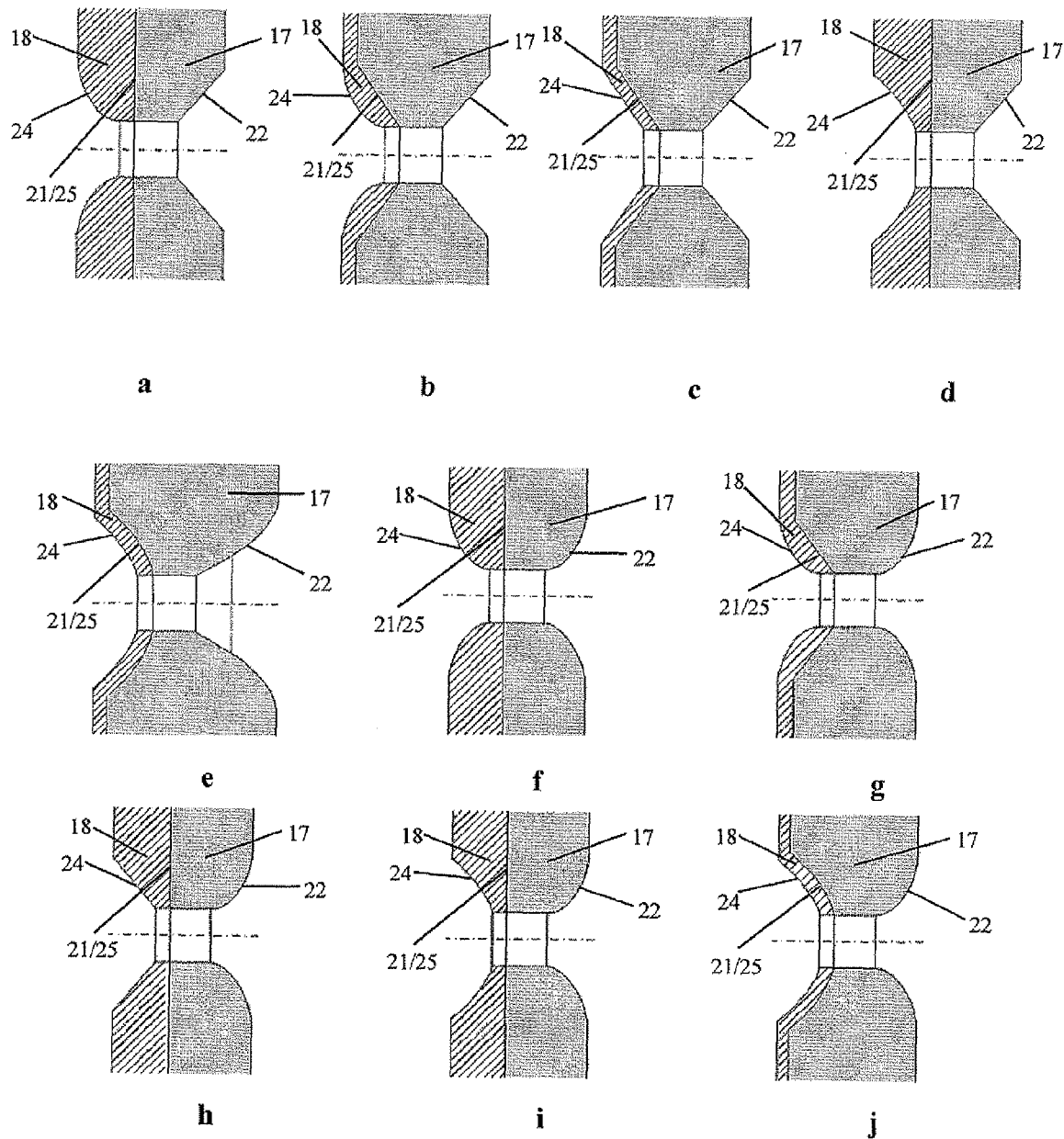
FIGS. 9a to 9j are schematic, structural illustrations of preferable embodiments of the microscopic hole sensor assembly of the present invention, respectively.

At the same time, the combination of the flow-guiding plate and the microscopic hole plate should satisfy the requirements as to uniform distribution of structural stress. For example, the flow-guiding plate with a concave front end surface should not be combined with the microscopic hole plate with a convex front end surface. The front end surface 21 of the microscopic hole plate closely engages with the rear end surface 25 of the flow-guiding plate, and the microscopic hole pipeline 23 of the microscopic hole plate is coaxial with and has identical aperture dimension to the microscopic hole pipeline 26 of the flow-guiding plate, forming a uniform and smooth pipeline curved surface 27, as shown in FIG. 7a. The downstream curved surface 19 of the fixed seat 2 may adopt a bugle-shaped, circular, convex, conical or concave whirly curved surface in order to ensure the fixed seat downstream curved surface to match the sensor assembly and form a stable liquid flow line 20. Both the above end surfaces 22, 24 and the distended downstream surface 19 may adopt a combination of curved surfaces, i.e., a conical surface in combination with a bugle-shaped surface, as shown in FIG. 9.

Figure 10A:
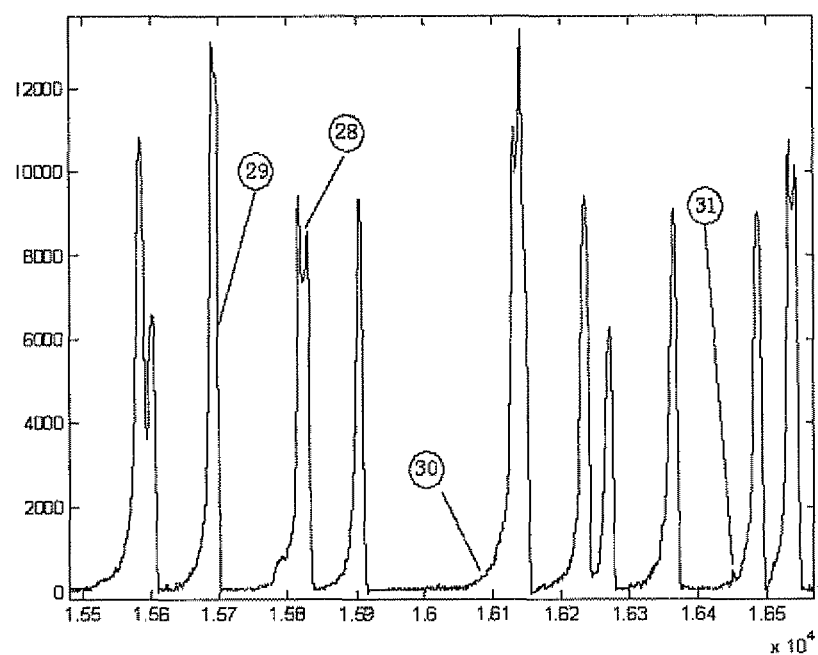
Figure 10B:
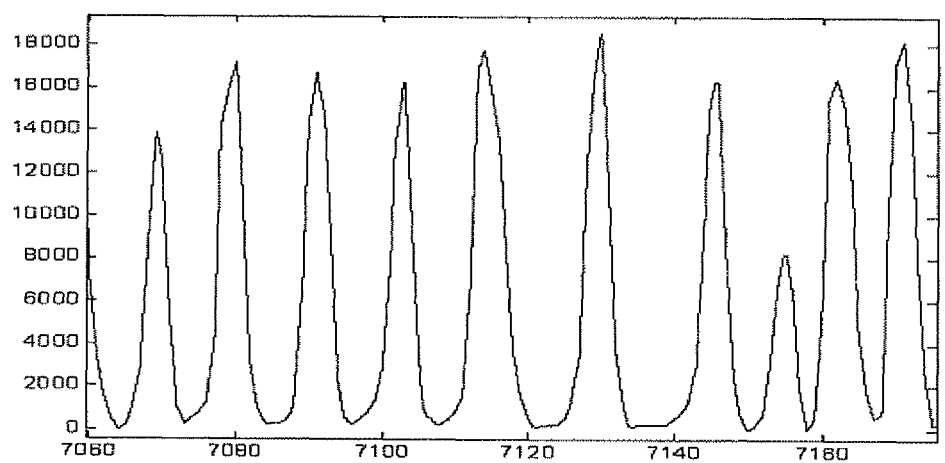
FIG. 10b is a diagram showing volumes of the blood cells using the present measuring technique.

The experimental result shows that the device according to the present invention significantly improves the signal quality. A comparison of the experimental results is shown in FIGS. 10a and 10b. FIG. 10a is a waveform diagram of the blood cell counting signals. As seen from the figure, the signals suffer from multiple M-shaped waves 28, steep rear edges 29, slow rise edge 30, and undue signal noise 31. FIG. 10b is a waveform diagram of the signals achieved by counting and detecting using the present invention microscopic hole sensor assembly. Apparently, signal quality of the cells is markedly enhanced.

In summary, the device for detecting and counting blood cells according to the present invention comprises the microscopic hole assembly 1 and the fixed seat 2 with a bugle-shaped downstream surface 19. This device improves the flow field characteristics and the speed feature at the microscopic hole inlet and outlet, thus perfecting the pulse signals of the cells. At the same time, the microscopic hole sensor assembly consisting of a combination of the microscopic hole plate 17 and the flow-guiding plate 18 effectively improves the electric field distribution and flow field characteristics at the inlet of the sensor microscopic hole, restrains the cells from entering into the orifice area close to the edge of the sensor microscopic hole sensitivity area, and increases the speed of the particles when entering into the sensor microscopic hole sensitivity area. Furthermore, as the rear end surface 22 of the outlet of the microscopic hole plate is a bugle-shaped whirly curved surface and the downstream surface 19 of the fixed seat 2 is bugle-shaped and distended, consequently the characteristics of the flow field are further optimized, such that the cell particle refluence is effectively restrained, thus reducing the harmful effect upon the detection result caused by false pulses due to particle refluence.

Moreover, the structure and manufacture of the microscopic hole sensor assembly according to the present invention are simple, and moreover the microscopic hole sensor thereof has a greatly shortened length in terms of the effective orifice area in the microscopic hole. Thus, it is less likely to cause jam at the counting process. As such, the present invention provides an improved low-cost and effective microscopic hole sensor assembly over the prior art.

It is to be understood, however, that even though numerous characteristics and advantages of the present invention have been set forth in the foregoing description, together with details of the structure and function of the invention, the disclosure is illustrative only and shall not be considered as a limitation to the scope of the present invention. For example, the device of the present invention is not only useful for detecting blood cells, but also for detecting body fluids such as emiction, etc. Those skilled in the art may understand that changes may be made in detail, especially in matters of shape, size, and arrangement of parts within the principles of the invention to the full extent indicated by the broad general meaning of the terms in which the appended claims are expressed.

What is claimed is:

1. A device for determining one or more parameters of particles in a conductive solution, comprising:
    a front pool;
    a back pool spaced from the front pool; and
    a microscopic hole sensor assembly, comprising:
        a microscopic hole plate with a microscopic hole defined therein, the microscopic hole plate comprising an inlet on a front pool side and an outlet on a back pool side and communicating the front pool with the back pool;
        a first electrode and a second electrode respectively arranged in the front pool and the back pool configured for conducting an electric current between the front pool and the back pool via the conductive solution passing through the microscopic hole from the inlet to the outlet;
        a processing circuit connecting the first electrode and the second electrode, the processing circuit being configured for detecting the electric current or one or more changes in an electric field caused by the electric current and outputting a detection result, wherein
        an electrically conductive material that is a part of or is attached to the inlet forms at least a part of the first electrode and at least in part a flow-guiding surface which gradually narrows from the front pool side towards the back pool side,
        the outlet comprises or attaches to a fixed seat with a downstream surface gradually distending and extending towards the back pool to form an effective orifice configured for determining the one or more parameters of the particles in the microscopic hole, wherein the fixed seat, through which the particles exit the microscopic hole plate, does not support electrically conductive materials, and a first center axis of the first electrode or a second center axis of the second electrode substantially aligns with a third center axis of the microscopic hole.

2. The device as claimed in claim 1, wherein the microscopic hole sensor assembly further comprises a flow-guiding plate positioned at the end surface of the inlet, a front end surface of which plate functions as the flow-guiding surface, and a rear end surface of which is matchingly assembled with the front end surface of the microscopic hole plate to form an effective orifice area configured for accelerating liquid flow at a corresponding position within the microscopic hole.

3. The device as claimed in claim 2, wherein the flow-guiding plate is a good electric conductor and is configured to comprise the first electrode in the front pool.

4. The device as claimed in claim 3, wherein the microscopic hole sensor assembly further comprises the fixed seat that is positioned at an end surface of the outlet on the back pool side, wherein the fixed seat comprises the downstream surface gradually distending and extending towards the back pool.

5. The device as claimed in claim 4, wherein the back pool is configured to be a sealed pool; a negative pressure extracting outlet and the second electrode therein are outwardly positioned and aligned with the microscopic hole; and at least one inlet is positioned along the downstream surface for washing the back pool.

6. The device as claimed in claim 5, wherein a thickness of the effective orifice area of the microscopic hole plate is 1.1 to 4 times of that of the flow-guiding plate.

7. The device as claimed in claim 6, wherein each of the flow-guiding surface and the downstream surface is configured to comprise a bugle-shaped, circular, convex, conical, or concave whirly curved surface.

8. A microscopic hole sensor assembly used in a device for determining one or more parameters of particles, the device comprising:
a front pool and a back pool spaced from each other, the microscopic hole sensor assembly being positioned between the front pool and the back pool and comprising:
a microscopic hole plate with a microscopic hole defined therein, the microscopic hole plate comprising an inlet on a front pool side and an outlet on a back pool side and communicating the front pool with the back pool;
a first electrode and a second electrode respectively arranged in the front pool and the back pool and configured for conducting an electric current between the front pool and the back pool via a conductive solution passing through the microscopic hole from the inlet to the outlet; and
a processing circuit connecting the first electrode and the second electrode, the processing circuit being configured for detecting the electric current or one or more changes in an electric field caused by the electric current and outputting a detection result, wherein
an electrically conductive material that is a part of or is attached to the inlet forms at least a part of the first electrode and at least in part a flow-guiding surface which gradually narrows from the front pool side to the back pool side so as to form an effective orifice configured for determining the one or more parameters of the particles in the microscopic hole,
the outlet comprises or attaches to a fixed seat with a downstream surface gradually distending and extending towards the back pool, wherein the fixed seat, through which the particles exit the microscopic hole plate, does not support electrically conductive materials, and
a first center axis of the first electrode or a second center axis of the second electrode is aligned with a third center axis of the microscopic hole.

9. The microscopic hole sensor assembly as claimed in claim 8, wherein a rear end of the outlet comprises a first downstream surface gradually distending and extending towards the back pool.

10. The microscopic hole sensor assembly as claimed in claim 9, wherein the microscopic hole sensor assembly further comprises a flow-guiding plate positioned at the front end of the inlet, a front end of the flow-guiding plate functions as the flow-guiding surface, while the rear end surface of which is matchingly assembled with the front end of the microscopic hole plate to form an effective orifice area configured for accelerating liquid flow at a corresponding position within the microscopic hole.

11. The microscopic hole sensor assembly as claimed in claim 10, wherein the flow-guiding plate comprises an electrically conductive material and is configured to comprise the first electrode in the front pool.

12. The microscopic hole sensor assembly as claimed in claim 11, wherein the microscopic hole sensor assembly further comprises the fixed seat that is positioned on an end surface at the rear end of the outlet on the back pool side, wherein the fixed seat comprises the downstream surface gradually distending and extending outwardly from the end surface of the outlet.

13. The microscopic hole sensor assembly as claimed in claim 12, wherein each of the flow-guiding surface and the downstream surface is configured to comprise a bugle-shaped, circular, convex, conical, or concave whirly curved surface.

14. A microscopic hole sensor assembly used in a device for determining parameters of particles, the device comprising:
a front pool and a back pool spaced from each other, the microscopic hole sensor assembly being positioned between the front pool and the back pool;
a microscopic hole plate with a microscopic hole defined therein, the microscopic hole plate comprising an inlet on a front pool side and an outlet on a back pool side and communicating the front pool with the back pool;
a first electrode and a second electrode respectively arranged in the front pool and the back pool and configured for conducting an electric current between the front pool and the back pool via a conductive solution passing through the microscopic hole from the inlet to the outlet; and
a processing circuit connecting the first electrode and the second electrode, the processing circuit being configured for detecting the electric current or one or more changes in an electric field caused by the electric current and outputting a detection result, wherein
an electrically conductive material that is a part of or is attached to the inlet forms at least a part of the first electrode and at least in part a flow-guiding surface which gradually narrows from the front pool side towards the back pool side, and
the outlet comprises a downstream surface which gradually distends and extends from the front pool side to the back pool side to form an effective orifice configured for detection in the microscopic hole, wherein the fixed seat, through which the particles exit the microscopic hole plate, does not support electrically conductive materials, and a first center axis of the first electrode or a second center axis of the second electrode is aligned with a third center axis of the microscopic hole.

15. The microscopic hole sensor assembly as claimed in claim 14, wherein the microscopic hole sensor assembly further comprises the fixed seat that is positioned on an end surface on the back pool side of the outlet, wherein the fixed seat comprises the downstream surface gradually distending and extending outwardly from the rear end of the outlet.

16. The microscopic hole sensor assembly as claimed in claim 15, wherein the downstream surface is configured to comprise a bugle-shaped circular, convex, conical, or concave whirly curved surface.

17. The microscopic hole sensor assembly as claimed in claim 16, wherein both the first center axis and the second center axis are aligned with the third center axis of the microscopic hole.

18. The device of claim 1, wherein the first electrode and the second electrode are configured to align with an imaginary line connecting the first center axis of the first electrode and the second center axis of the second electrode with the third center axis of the microscopic hole.

19. The device of claim 1, wherein the conductive solution flows from the inlet to the outlet due to a negative pressure in the back pool.

20. The device of claim 1, wherein the first electrode comprises an integral part of the flow-guiding surface.

* * * * *